US008883862B2

(12) United States Patent
Ho et al.

(10) Patent No.: US 8,883,862 B2
(45) Date of Patent: Nov. 11, 2014

(54) METHOD FOR CONTROLLED RELEASE OF PARATHYROID HORMONE FROM CROSS-LINKED HYALURONIC ACID HYDROGEL

(75) Inventors: Mei-Ling Ho, Kaohsiung (TW); Rajalakshmanan Eswaramoorthy, Kaohsiung (TW); Shun-Cheng Wu, Kaohsiung (TW); Gwo-Jaw Wang, Taipei (TW); Je-Ken Chang, Kaohsiung (TW); Yin-Chih Fu, Kaohsiung (TW); Cherng-Chyi Tzeng, Kaohsiung (TW); Hui-Ting Chen, Kaohsiung (TW); Yao-Hsien Wang, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 0 days.

(21) Appl. No.: 13/349,533

(22) Filed: Jan. 12, 2012

(65) Prior Publication Data
US 2013/0183349 A1 Jul. 18, 2013

(51) Int. Cl.
*A61K 38/02* (2006.01)
*A61P 19/04* (2006.01)
*A61K 8/00* (2006.01)
*A61K 38/16* (2006.01)

(52) U.S. Cl.
CPC ........................................ *A61K 38/16* (2013.01)
USPC .................................. 514/777; 514/2; 514/12

(58) Field of Classification Search
None
See application file for complete search history.

(56) References Cited

U.S. PATENT DOCUMENTS

| | | | | |
|---|---|---|---|---|
| 2010/0160229 A1* | 6/2010 | Ho et al. | ............................ | 514/12 |
| 2010/0204102 A1* | 8/2010 | Akiyoshi et al. | ................. | 514/12 |
| 2011/0212901 A1* | 9/2011 | Akiyoshi et al. | .............. | 514/20.9 |
| 2011/0305766 A1* | 12/2011 | Ho et al. | ........................ | 424/497 |
| 2012/0003176 A1* | 1/2012 | Huang et al. | ................ | 424/78.27 |

OTHER PUBLICATIONS

Barbucci R. et al., Hyaluronic acid hydrogel in the treatment of osteoarthritis. Dec. 2002, Biomaterials, 23(23): 4503-13.*
Inoue A., et al., The therapeutic effects of basic fibroblast growth factor contained in gelatin hydrogel microspheres on experimental osteoarthritis in the rabbit knee. Jan. 2006, Arthritis Rheum, 54(1): 264-70.*
Inoeu et al. "The therapeutic effects of basic fibroblast growth factor contained in gelatin hydrogel microspheres on experimental osteoarthritis in the rabbit knee." Arthritis Rheum (Jan. 2006) 54(1): 264-70.*
Barbucci et al. "Hyaluronic acid hydrogel in the treatment of osteoarthritis." Biomaterials. (Dec. 2002) 23(23): 4503-13).*
Eswaramoorthy et al (Jan. 13, 2011) "A pilot study on sustained release of PTH (1-34) from encapsulated injectable photocrosslinked hyaluronan hydrogel" (Jan. 13, 2011) Presented at the Annual Meeting of the Orthopaedic Research Society.*
Program Book for the Annual Meeting of the Orthopaedic Research Society on Jan. 13, 2011.*
Deal, C. et al. "Recombinant human PTH 1-34 (Forteo): An anabolic drug for osteoporosis." (Jul. 2003) Cleveland Clinic Journal of Medicine 70:7, 585-601.*
Eli Lilly and Company. Product Insert for FORTEO (teriparatide [rDNA origin] injection (copyright 2002, 2012).*
Ho, Mei-Ling et al. "Development of the injectable controlled release PTH(1-34)/HA hydrogel for intro-articular treatment of osteoarthritis" (Sep. 3, 2010) Powerpoint presented at internal lab meeting.*
Kim et al ("Hydrogel design for cartilage tissue engineering: A case study with hyaluronic acid" (Dec. 2011) Biomaterials 32(34): 8771-8782).*
Oudshoorn et al ("Synthesis of methacrylated hyaluronic acid with tailored degree of substitution" (2007) Polymer 1915-1920).*
Chemical structure for Methacrylic acid (Sigma Aldrich Catalog, downloaded Jun. 6, 2013 from http://www.sigmaaldrich.com/Graphics/COfAInfo/SigmaSAPQM/SPEC/15/155721/155721-BULK_ALDRICH_.pdf).*
Chemical Structure for Methacryloyl chloride (Sigma Aldrich Catalog, downloaded Jun. 6, 2013 from http://www.sigmaaldrich.com/catalog/product/fluka/64120?lang=en&region=US).*
Deal et al (Cleveland Clinic Journal of Medicine (Jul. 2003) 70:7, 585-601).*
Eli Lilly and Company (Product Insert for FORTEO (teriparatide [rDNA origin] injection (copyright 2002, 2012), p. 7).*
Chang, J.K., et al., Parathyroid hormone 1-34 inhibits terminal differentiation of human articular chondrocytes and osteoarthritis progression in rats. Arthritis Rheum, 2009. 60(10): p. 3049-60.

* cited by examiner

*Primary Examiner* — Karlheinz R Skowronek
*Assistant Examiner* — Mindy Newman
(74) *Attorney, Agent, or Firm* — Hannah M. Tien (57) ABSTRACT

A method for locally controlled release of an effective amount of PTH(1-34) by a hyaluronic acid based hydrogel that can injected intra-articularly for the treatment of osteoarthritis is provided.

11 Claims, 8 Drawing Sheets

METHOD FOR CONTROLLED RELEASE OF PARATHYROID HORMONE FROM CROSS-LINKED HYALURONIC ACID HYDROGEL

FIELD OF THE INVENTION

The present invention relates to a method for controlled release of an effective amount of parathyroid hormone in a subject suffers from osteoarthritis by a cross-linked methacrylated-hyaluronic acid (CLMH) hydrogel, and use thereof.

BACKGROUND OF THE INVENTION

Parathyroid hormone 1-34 (PTH(1-34)) is a 34 amino acids polypeptide and FDA approved clinical drug for the treatment of osteoporosis and bone disorders. Recently, it was found that PTH(1-34) acts on articular chondrocytes to suppress their terminal differentiation, and it can also suppress papain-induced osteoarthritis (OA) in rats (Chang, J. K., et al., Parathyroid hormone 1-34 inhibits terminal differentiation of human articular chondrocytes and osteoarthritis progression in rats. Arthritis Rheum, 2009. 60(10): p. 3049-60). But, the treatments require the administration of drug once in 3 days, which makes more sufferings and inconvenient for patient undergoing the treatment. Thus, there is a need to develop a new controlled releasing carrier formulation of a parathyroid hormone peptide in order to reduce the patient suffering and that has suitable bioavailability such that therapeutic level can be achieved for effective treatment of PTH related disorders.

In pharmacology, bioavailability (BA) is a subcategory of absorption and is used to describe the fraction of an administered dose of unchanged drug that reaches the systemic circulation, one of the principal pharmacokinetic properties of drugs. By definition, when a medication is administered intravenously, its bioavailability is 100%. However, when a medication is administered via other routes (such as orally), its bioavailability generally decreases (due to incomplete absorption and first-pass metabolism) or may vary from patient to patient. Bioavailability is one of the essential tools in pharmacokinetics, as bioavailability must be considered when calculating dosages for non-intravenous routes of administration.

In recent years, many methods have been investigated for the administration of PTH to the treatment in clinical trials. A recent reported method emphasized the oral administration of PTH(1-34) showed biologically active. However, the bioavailability of PTH is only 5% and 2.1%, in comparison to subcutaneous administration. On the other hand, the pulmonary route has shown 40% and 34% bioavailabilities of PTH (1-34) by means of intratracheal instillation or inhalation of dry powders, respectively. In addition to that for intermittent PTH delivery include programmed administration by osmotic pump and pulsatile transdermal administration. Both of these methods showed equivalent anabolic actions of PTH on bone like subcutaneous administration. Human PTH(1-38) has also shown similar results. There is relatively little work focusing on local delivery of PTH. Notably, these few studies indicated that PTH administered locally via a direct gene delivery which was found to be beneficial in the treatment of bony defects.

PTH(1-34), also called teriparatide, is commercially available in market under the brand name FORTEO® manufactured by Eli Lilly, Indianapolis, Ind., for the treatment of osteoporosis in postmenopausal women with high risk of fracture. This drug is administered by once in daily subcutaneous injection of PTH(1-34) formulations (acetate buffer, mennitol, and m-cresol in water, pH 4). However, many people had adverse response to injections, and thus become non-compliance with the prescribed dosing of the PTH. Therefore, an appropriate drug carrier is required to prolong the injection interval and sustained release of PTH(1-34) over a time period.

SUMMARY OF THE INVENTION

The present invention provides a method for local delivery of PTH(1-34) with an effective concentration using an injectable photo-crosslinked methacrylated hyaluronic acid hydrogel that can control release of PTH(1-34) for at least 10 days in cartilage clinical applications.

DETAIL DESCRIPTION OF THE INVENTION

Osteoarthritis (OA), also known as degenerative arthritis or degenerative joint disease is a group of mechanical abnormalities involving degradation of joints, including articular cartilage and subchondral bone. Symptoms may include joint pain, tenderness, stiffness, locking, and sometimes an effusion. A variety of causes—hereditary, developmental, metabolic, and mechanical—may initiate processes leading to loss of cartilage. When bone surfaces become less well protected by cartilage, bone may be exposed and damaged. As a result of decreased movement secondary to pain, regional muscles may atrophy, and ligaments may become more lax.

OA commonly affects the hands, feet, spine, and the large weight bearing joints, such as the hips and knees, although in theory, any joint in the body can be affected. As OA progresses, the affected joints appear larger, are stiff and painful, and usually feel better with gentle use but worse with excessive or prolonged use, thus distinguishing it from rheumatoid arthritis.

Osteoarthritis is easily to decrease glycosaminoglycan (GAG) and collagen levels, but the mechanism remains unclear. During OA progression, articular chondrocytes undergo terminal differentiation and decrease the level of GAG and type II collagen (COL. II), but increase the level of type X collagen (COL. X), which is similar as those during endochondral ossification.

Natural and synthetic carriers have been developed as an effective method to control the release of the encapsulated protein and to protect them from degradation. However, the excellent biocompatibility and biodegradability through natural pathways make natural carriers are more appropriate for the application of drug delivery. Hyaluronic acid (HA) is the natural polymer and one of the major physiological components in the articular cartilage matrix. In particular, it is abundant in synovial fluid. HA has been an agent to relief osteoarthritis symptoms. Therefore, it is hypothesized that using HA based hydrogel is more suitable for PTH controlled release for prolonged duration in cartilage clinical applications. Here in, the invention is for the method to control release of PTH with therapeutic concentration and bioavailability.

The present invention provides a method for controlled release of parathyroid hormone (PTH) in a subject suffers from osteoarthritis, comprising:
(a) providing a hydrogel comprising a cross-linked methacrylated-hyaluronic acid (CLMH) and PTH; and
(b) administering the hydrogel to a joint of a subject suffers from osteoarthritis;
wherein the hydrogel controls release of an effective amount of PTH for at least 10 days.

In the present invention, the osteoarthritis is caused by terminal differentiation of chondrocytes, and it commonly affects knee joints, hip joints, spine joints or finger joints.

In the present invention, the methacrylated-hyaluronic acid is cross-linked by irradiating of UV light and the PTH is encapsulated in same step. This forms a hydrogel with a three dimensional structure and it controls release of an effective amount of PTH(1-34).

In the general embodiment of the present invention, the hydrogel controls release of an effective amount of PTH(1-34) for 10 to 15 days. In the preferred embodiment, the hydrogel controls release of an effective amount of PTH(1-34) for 10 to 12 days.

In the general embodiment of the present invention, the concentration of released PTH(1-34) is from about $1\times10^{-9}$ M to about $5\times10^{-7}$ M. In the preferred embodiment, the concentration of released PTH(1-34) is from about $2\times10^{-9}$ M to about $5\times10^{-8}$ M. In the more preferred embodiment, the concentration of released PTH(1-34) is from about $4.3\times10^{-9}$ M to about $1.23\times10^{-8}$ M.

In the present invention, the hydrogel is injected intra-articularly for the treatment of osteoarthritis. In the preferred embodiment, the subject is a mammal. In the more preferred embodiment, the subject is a human.

EXAMPLES

Example 1

Hydrogel Preparation and Characterization

The hydrogel was fabricated by the photo-cross linking method. Briefly, 20 mg of methacrylated-hyaluronic acid (MeHA) was dissolved in 650 μL of stock solution (0.9% NaCl/4 mM HCl/0.1% BSA solution) and 100 μL of 0.07% (w/v) 12959 (Ciba specialty chemicals, Taiwan) was added to the solution. After complete dissolution, 250 μL of PTH(1-34) stock solution ($10^{-5}$ M) was added to the polymer solution and mixed completely. The mixture was transferred into glass syringe and exposed under UV light for 10 minutes. The resulting PTH/CLMH gel was washed with distilled water and then lyophilized. The morphology of the gel was examined using scanning electron microscopy (SEM) after gold coating of the samples on a stub.

The encapsulation and release kinetics are as follows: 200 μL of PTH(1-34)-loaded CLMH hydrogel (PTH/CLMH gel) suspended in 1 mL of 0.9% NaCl was crushed completely and collected the supernatant. Concentration of PTH(1-34) on the supernatant was measured using a commercially available PTH(1-34) ELISA kit following the manufacturer's instructions.

Figure 1:
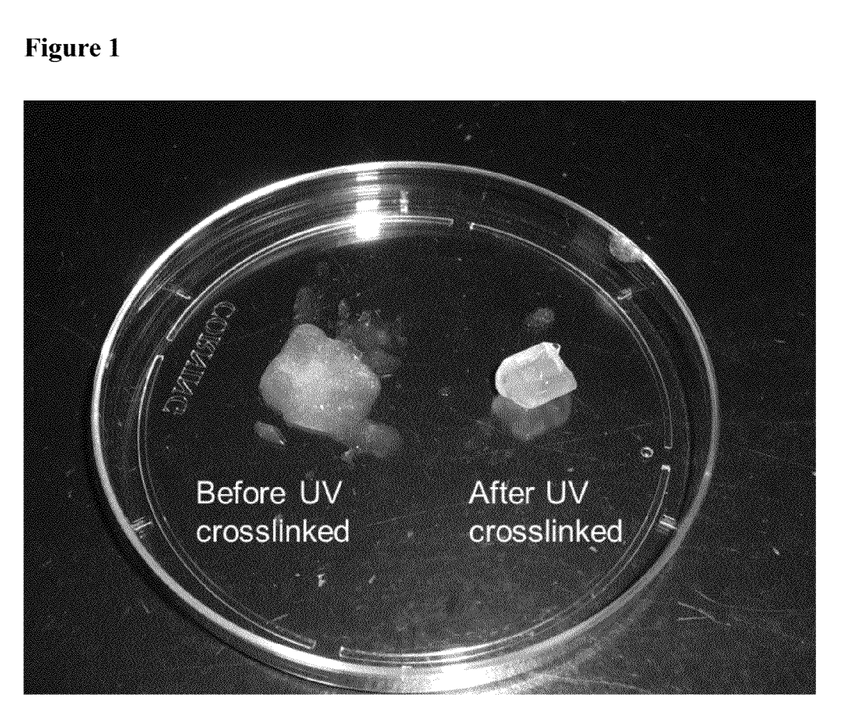
FIG. 1 shows the structure of the hyaluronic acid before (left) and after (right) UV light cross-linking.
Figure 2:
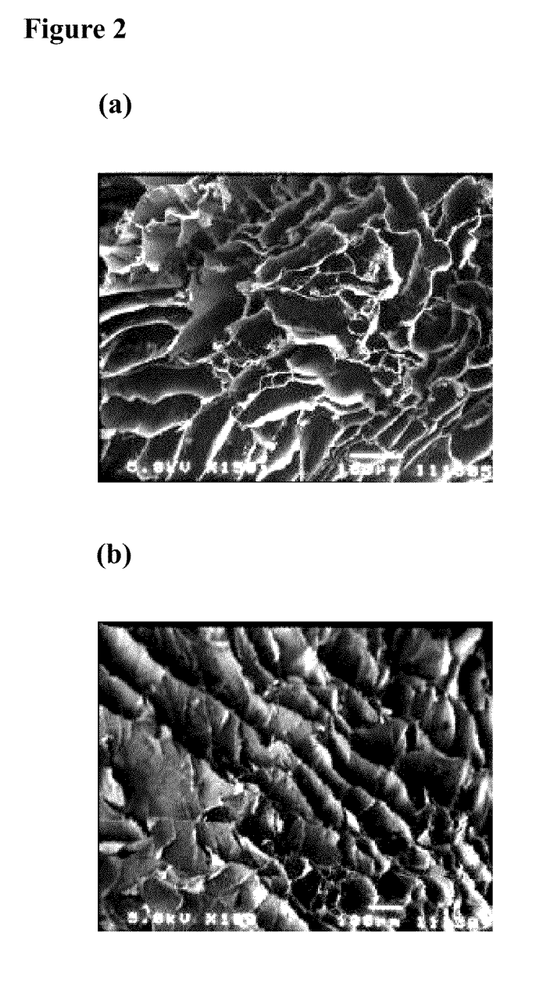
FIG. 2 shows the scanning electron microscopic images of CLMH hydrogels, (a) is horizontal and (b) is vertical section of the hydrogel.
Figure 3:
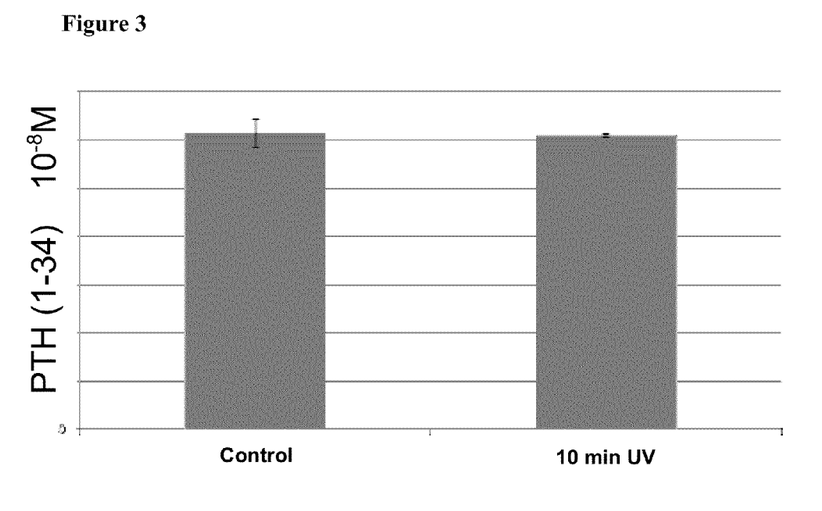
FIG. 3 shows the stability of PTH(1-34) under UV exposure.

The structures of the HA before and after UV light crosslinking are shown in FIG. 1. The SEM observation emphasized that the hydrogel has smooth morphology with highly porous honeycomb like structure (FIG. 2). The hydrogel showed 99% encapsulation efficiency and the swelling test showed that the hydrogels have 152-162% swelling ratio (Table 1). The ELISA test confirmed that 10 minutes of UV exposure had no significant adverse effect on the stability of PTH(1-34) (FIG. 3).

TABLE 1

The swelling ratio and encapsulation of the hydrogel.

| CLMH | Swelling Ratio (%) | | Encapsulation (%) |
|---|---|---|---|
| | Day 1 | Day 2 | |
| 2% W/V | 152 | 162 | 99 |

Example 2

In Vitro PTH(1-34) Release

In vitro PTH(1-34) release profiles from PTH/CLMH hydrogel were determined as follows: 200 μL of hydrogel was suspended in 1 ml releasing mixture (0.9% NaCl and 0.1% BSA containing hyaluronidase (10 unit/mL), pH=7.4). The suspensions were incubated at 37° C. with shaking. At designated time interval, 750 μL release medium was collected by centrifugation and replaced with equal amount of fresh releasing mixture. The concentration of PTH(1-34) in the release medium was measured by using a PTH(1-34) ELISA kit with PTH antibody coated wells following the manufacturer's recommendations (Immutopics, San Clemente, Calif.). Triplicate wells were used for each time point (first 24 h). Absorbance measurements read at 450 nm recorded by a microtiter plate reader were used to calculate the PTH(1-34) concentration by the log-logit method using the GraphPad Prisms program (GraphPad Software, San Diego, Calif.) with a standard curve.

Figure 4:
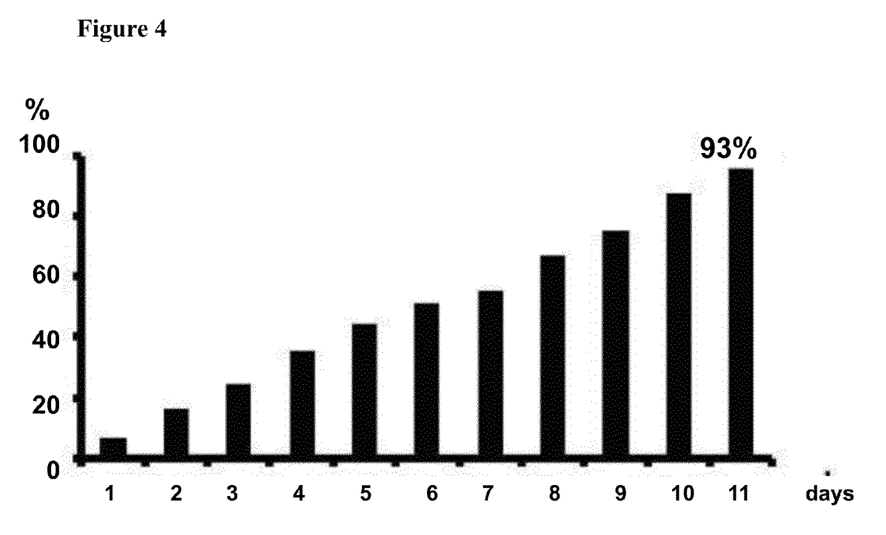
FIG. 4 shows the cumulative release profile of PTH(1-34) from CLMH hydrogel.
Figure 5:
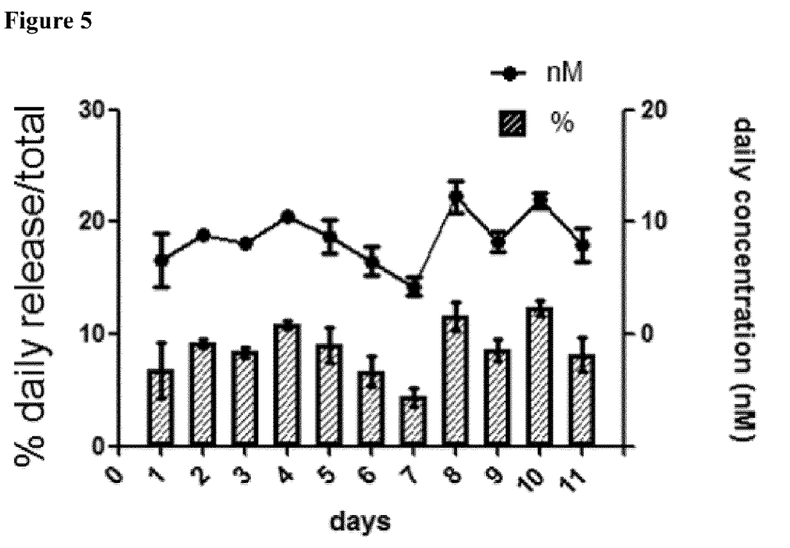
FIG. 5 shows the daily release profile of PTH(1-34) from CLMH hydrogel.

The release kinetic data from PTH(1-34) specific ELISA analysis showed that PTH/CLMH hydrogel released the PTH (1-34) for 11 days with desired concentration of 4.3~12.3 nM at 37° C. and at the $11^{th}$ day, the total releasing amount was 95% (FIGS. 4, 5). A recent report suggested that the effective dose of PTH(1-34) for the treatment of papain induced OA in rat was $10^{-8}$ M (Chang, J. K., et al., Parathyroid hormone 1-34 inhibits terminal differentiation of human articular chondrocytes and osteoarthritis progression in rats. Arthritis Rheum, 2009. 60(10): p. 3049-60) and the injection rate was once in three days for 4 weeks. So the hydrogel in the present invention can release the effective dose of PTH(1-34) for the treatment of OA.

Example 3

Bioactivity of Released PTH(1-34)

The activity of controlled released PTH(1-34) was determined by measuring cAMP contents in cells treated with released PTH(1-34). For these examples, the MC3T3-E1 (osteoblastic cells) was cultured in phenol red-free α-MEM supplemented with 10% fetal bovine serum and 50 mg/mL ascorbic acid. The Cells were seeded into 24-well plates at a density of 50,000 cells/well. 0.25 mM isobutylmethylxanthine was used to inhibit cAMP degradation and incubated with released PTH(1-34) for 20 mins. The cells were lysed directly in the medium by adding 0.1N HCl. Intracellular cAMP was measured using a commercially available immunoassay kit (cayman) following the manufacturer's instructions.

Statistical analysis: Three independent cultures for biochemical analysis were tested. Each example was repeated at least three times, and data (expressed as mean±SEM) from a representative example are shown. Statistical significance was evaluated by one-way analysis of variance (ANOVA), and multiple comparisons were performed by Student's t-test. A $p<0.05$ was considered significant.

Figure 6:
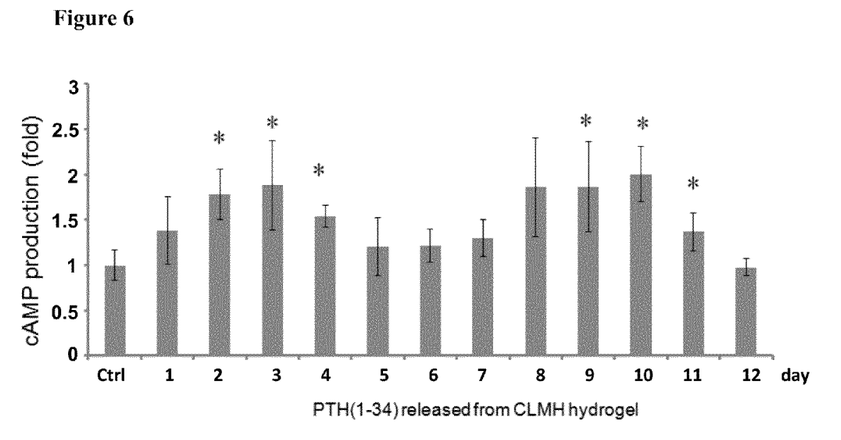
FIG. 6 shows the bioactivity of PTH(1-34) from PTH/CLMH hydrogel treated MC3T3-E1 cells.

The bioactivity data showed that the increased expression of cAMP in the released PTH(1-34) treated MC3T3-E1 cells at 2, 3, 4, 9, 10 and 11 days, indicating the released PTH(1-34) possessed bioactivity (FIG. 6).

Example 4

OA Induction and PTH(1-34) Treatment

Rats were divided into the following 2 groups: OA group (OA induction with or without PTH(1-34) treatment) (n=5), non-OA group (n=5) injected with vehicle without PTH(1-34) treatment and OA induction. The right knees were the study joints. OA was induced in the right knees of rats in the OA groups with intra-articular injections of 20 ul of 4% papain solution and 20 ul of 0.03M cysteine. The injections were given with a 23-gauge needle via the patellar tendon on days 1, 4, and 7 of the example. In the OA group, after OA induction, the right knees were injected intra-articularly with 40 ul of 10 nM PTH(1-34) every 3 days or PTH/CLMH or CLMH every 10 days until rats were sacrificed. In the non-OA group, the same treatments were performed but without OA induction. Rats from each group were sacrificed by $CO_2$ inhalation.

Histologic analysis: After rats were sacrificed, the knees were harvested, and the tibia plateaus with articular cartilage were collected and fixed with 10% neutral buffered formalin prior to histologic preparation. The samples were then decalcified in 0.05M EDTA. The decalcified tibia articular samples were paraffin embedded, and 5um microsections in the coronary plane were prepared. GAG was stained with Safranin O-fast green (1% Safranin 0 counterstained with 0.75% hematoxylin and then 1% fast green; Sigma) (dark color). Localized type II collagen was immunostained (dark color).

Immunohistochemistry: The tibia articular sections were rehydrated, and the endogenous peroxidase in tissue was blocked with 3% hydrogen peroxide. Samples were digested with enzymes for epitope retrieval before incubation with primary antibodies. The method for enzyme digestion was modified from that described previously. The optimal condition for enzyme digestion for type II collagen immunostaining was a mixture of 2.5% hyaluronidase and 1 mg/ml of Pronase in PBS (pH 7.4; Sigma) at 37° C. for 1 hour. Sections were then blocked with FBS for 1 hour and incubated with primary antibodies to type II collagen (mouse monoclonal antibody; Chemicon, Temecula, Calif.). The secondary antibodies were incubated for 30 minutes using biotin-labeled goat anti-mouse immunoglobulin for type II collagen (Dako, Carpinteria, Calif.) and horseradish peroxidase-conjugated streptavidin (Biocare Medical). Staining with a 3,3'-diaminobenzidine solution containing 0.01% hydrogen peroxide resulted in a dark color. Finally, sections were counterstained with hematoxylin and observed with a microscope.

Figure 7:
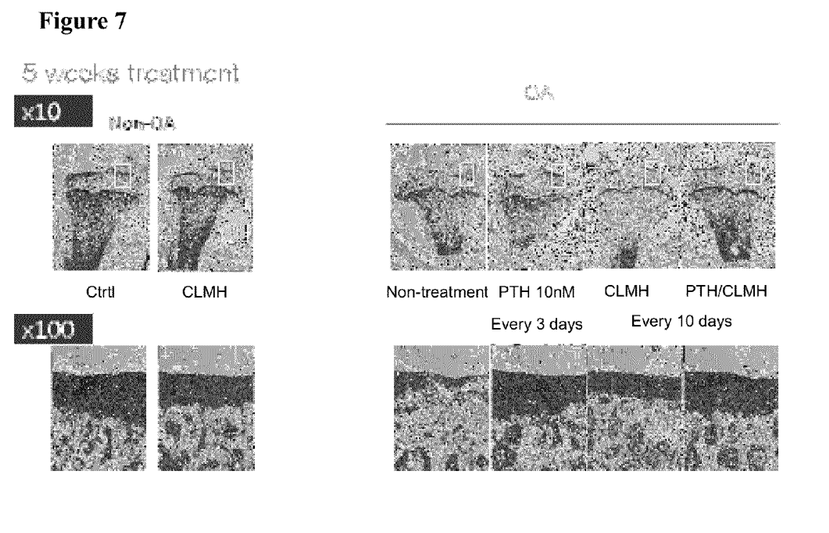
FIG. 7 shows the GAG expression from papain induced OA rats.
Figure 8:
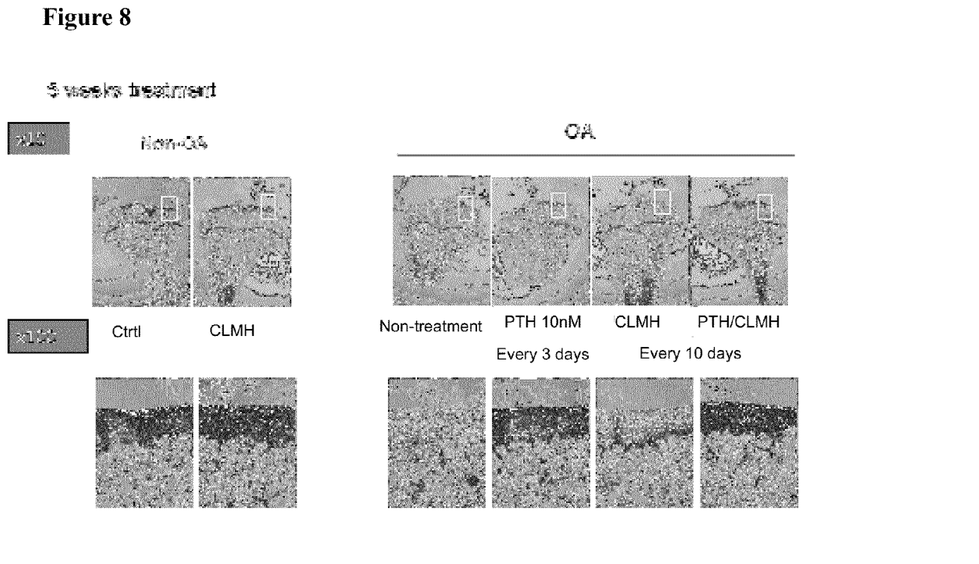
FIG. 8 shows the type II collagen expression from papain induced OA rats.

The level of GAG in normal and OA articular cartilage treated with PTH(1-34) was shown in FIG. 7. Treating with hydrogels once every 10 days for 35 days has no significant influence in normal articular cartilage. In OA group, the level of GAG was significantly reduced, and treating with PTH(1-34) 10 nM, CLMH hydrogel, PTH/CLMH hydrogel could reverse papain-induced OA changes by increasing GAG level. The level of type II collagen also showed similar pattern (FIG. 8). It is showed here that PTH/CLMH hydrogel has the same effect with PTH(1-34) in OA treatment.

These studies illustrate the feasibility of achieving controlled local delivery of PTH(1-34) and maintain their constant concentration by CLMH hydrogel encapsulation method. Therefore, the PTH(1-34) encapsulated CLMH hydrogel may be a potential carrier for PTH(1-34) delivery system, which can constantly deliver the PTH(1-34) for a period of time at effective range of concentration. Accordingly, the PTH(1-34) encapsulated HA hydrogel can be used to treat osteoarthritis.

What is claimed is:

1. A method for controlled release of parathyroid hormone (1-34) (PTH (1-34)) in a subject suffering from osteoarthritis, comprising:
    (a) providing a hydrogel consisting of a UV-irradiated cross-linked methacrylated-hyaluronic acid (CLMH) and PTH (1-34) in acid solution; and
    (b) administering the hydrogel to a joint of a subject suffering from osteoarthritis, wherein the hydrogel controls sustained-release of an effective amount of PTH (1-34).

2. The method of claim 1, wherein the osteoarthritis is caused by terminal differentiation of chondrocytes.

3. The method of claim 1, wherein the joint is a knee joint, hip joint, spine joint or finger joint.

4. The method of claim 1, wherein the UV-irradiated cross-linked methacrylated-hyaluronic acid encapsulates the PTH (1-34).

5. The method of claim 1, wherein the hydrogel has a three dimensional structure.

6. The method of claim 1, wherein the effective amount is from about $2 \times 10^{-9}$ M to about $5 \times 10^{-8}$ M.

7. The method of claim 1, wherein the effective amount is from about $4.3 \times 10^{-9}$ M to about $1.23 \times 10^{-8}$ M.

8. The method of claim 1, wherein the administration is intra-articular injection.

9. The method of claim 1, wherein the subject is a mammal.

10. The method of claim 9, wherein the mammal is a human.

11. The method of claim 1, wherein the effective amount is from about $1 \times 10^{-9}$ M to about $5 \times 10^{-7}$ M.

* * * * *